(12) United States Patent
Fang et al.

(10) Patent No.: US 10,994,039 B2
(45) Date of Patent: May 4, 2021

(54) STORAGE APPARATUS AND METHOD FOR IDENTIFYING A POSITION OF AN OBJECT

(71) Applicant: ASP GLOBAL MANUFACTURING GMBH, Schaffhausen (CH)

(72) Inventors: Yan Fang, Somerville, NJ (US); Nick N. Nguyen, Silverado, CA (US); Mohammad Khair, Somerville, NJ (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 347 days.

(21) Appl. No.: 15/854,372

(22) Filed: Dec. 26, 2017

(65) Prior Publication Data
US 2019/0192712 A1 Jun. 27, 2019

(51) Int. Cl.
| | | |
|---|---|---|
| *A61L 2/24* | (2006.01) | |
| *A61B 1/005* | (2006.01) | |
| *A61L 2/26* | (2006.01) | |
| *A61B 1/00* | (2006.01) | |
| *A61B 90/70* | (2016.01) | |
| *A61L 2/28* | (2006.01) | |
| *A61B 1/12* | (2006.01) | |

(52) U.S. Cl.
CPC ............ *A61L 2/24* (2013.01); *A61B 1/00059* (2013.01); *A61B 90/70* (2016.02); *A61L 2/26* (2013.01); *A61L 2/28* (2013.01); *A61B 1/12* (2013.01); *A61L 2202/14* (2013.01); *A61L 2202/24* (2013.01)

(58) Field of Classification Search
CPC .............................. A61L 2/24; A61B 1/00059
See application file for complete search history.

(56) References Cited

U.S. PATENT DOCUMENTS

| 6,663,202 B2 | 12/2003 | Spann | |
|---|---|---|---|
| 7,055,833 B2 | 6/2006 | Wixted et al. | |
| 2013/0144428 A1* | 6/2013 | Irwin | ................... B65G 1/0485 700/218 |

(Continued)

FOREIGN PATENT DOCUMENTS

| EP | 1570865 A2 | 9/2005 |
|---|---|---|
| EP | 1935366 A1 | 6/2008 |
| WO | WO 2006/060781 A1 | 6/2006 |

OTHER PUBLICATIONS

Custom Endoscopy Carts, accessed at https://www.phswest.com/products/endoscopy-carts/?gclid . . . , PHS West, Inc., 2018, 10 pages.

(Continued)

*Primary Examiner* — Kevin Joyner
(74) *Attorney, Agent, or Firm* — K&L Gates LLP

(57) ABSTRACT

An apparatus and method are disclosed for identifying the position of an object that is, or will be, used in a sterilization process. The apparatus comprises at least two containers and each container has a cavity configured to receive the object. At least one visual indicator corresponds to each container. A programmable hardware device is configured to receive an identifier. Responsive to receipt of the identifier, the programmable hardware device is configured to indicate a position of at least one of the containers that corresponds to the identifier utilizing the visual indicator.

23 Claims, 6 Drawing Sheets

(56) References Cited

U.S. PATENT DOCUMENTS

2015/0007619 A1* 1/2015 Finney .................... E05B 47/00
 70/58
2017/0333105 A1* 11/2017 Newell .................. A61B 18/02
2018/0040181 A1* 2/2018 Groeger ............. G07C 9/00912

OTHER PUBLICATIONS

Endoscope Trolley—All Medical Device Manufacturers, accessed at http://www.medicalexpo.com/medical-manufacturer/endoscope-trolley-3272.html, Medical Expo, 2018, 23 pages.

* cited by examiner

STORAGE APPARATUS AND METHOD FOR IDENTIFYING A POSITION OF AN OBJECT

FIELD OF THE INVENTION

The present disclosure relates to storage apparatus and methods for identifying a position of an object.

BACKGROUND

Various medical devices are used in numerous procedures in the medical field. These devices are as varied as the treatments themselves. As such, proper care of these devices is critical for efficiency of application and the proper corresponding treatment of the patient.

After a medical device, such as an endoscope, is used, the medical device is cleaned, disinfected, and/or sterilized in order to prepare the medical device for its next use. The cleaning, disinfecting, and/or sterilizing may include attaching the medical device to a re-processing machine, such as an automated endoscope re-processor or an endoscope cleaner and re-processor, using a connector (a tubing, a fitting, etc.). After the cleaning, disinfecting, and/or sterilization process is executed, the medical device is ready for another use. While the medical device is non-sterile and/or being cleaned, disinfected, and/or sterilized, the medical device is typically unavailable for use, resulting in downtime of the medical device.

SUMMARY

In one aspect, the present disclosure provides a storage apparatus for identifying a position of an object in a sterilization process. The apparatus comprises at least two containers. Each container has a cavity configured to receive the object. At least one visual indicator corresponds to each container. The apparatus further comprises a programmable hardware device configured to receive an identifier. Responsive to receipt of the identifier, the programmable hardware device is configured to indicate a position of at least one of the containers that corresponds to the identifier utilizing the visual indicator.

In another aspect, a method is provided for identifying the position of and/or retrieving an object that is, or will be, used in a sterilization process. A storage apparatus that comprises at least two containers is prepared. Each container has a cavity configured to receive the object. At least one visual indicator corresponds to each container. Responsive to receipt of an identifier, a position of at least one of the containers that corresponds to the identifier is indicated utilizing the visual indicator. At least one of the objects is retrieved from the container as indicated by the visual indicator.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description taken in conjunction with the accompanying drawings, wherein.

Corresponding reference characters indicate corresponding parts throughout the several views. The exemplifications set out herein illustrate certain embodiments, in one form, and such exemplifications are not to be construed as limiting the scope of the examples in any manner.

DETAILED DESCRIPTION

Figure 1:
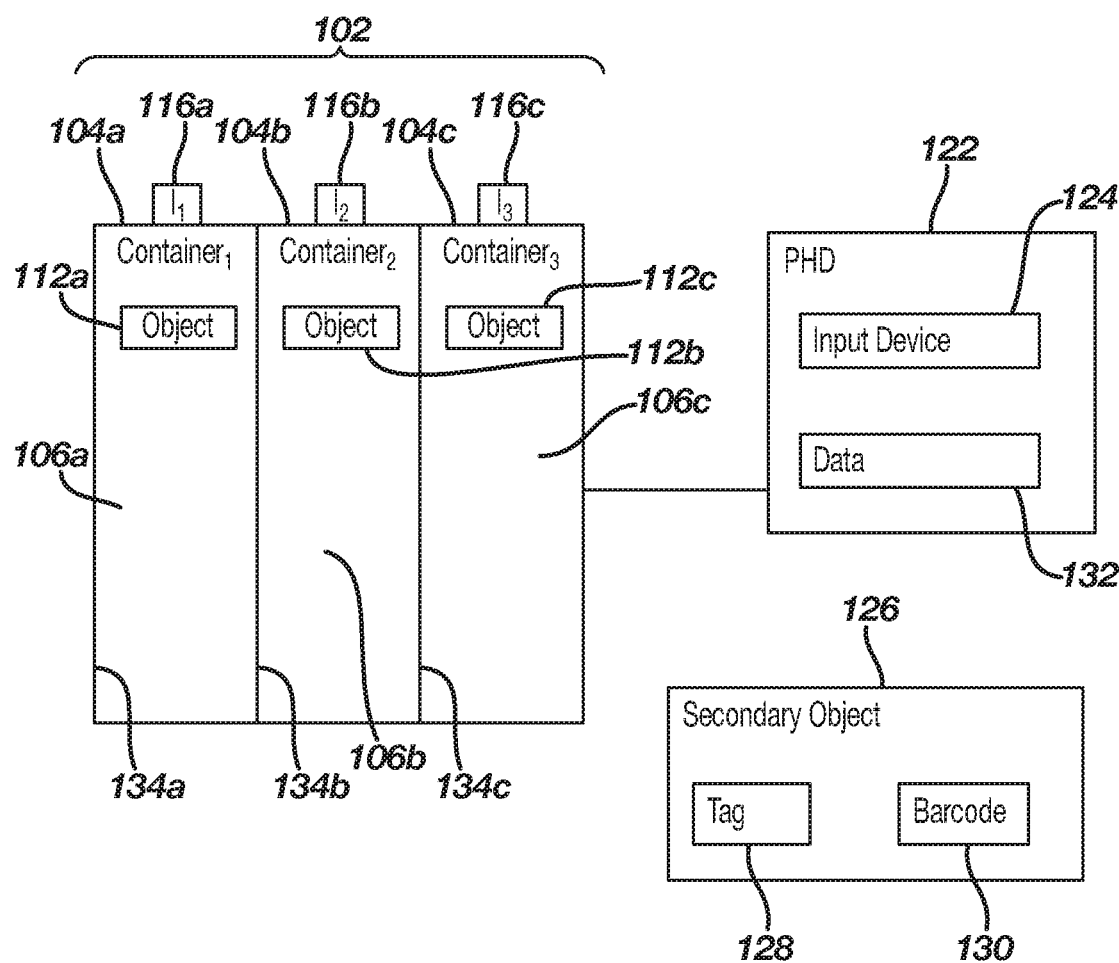
FIG. 1 is a plan view illustrating a storage apparatus for identifying a position of an object.

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification such that amending to expressly recite any such sub-ranges would comply with the requirements of 35 U.S.C. § 112 and 35 U.S.C. § 132(a).

Various medical devices are employed for procedures in the medical field. For example, when the medical device is an endoscope, these devices are commonly employed to examine the interior of a hollow organ or cavity of the body. Accordingly, medical devices may allow for various connectors to achieve a specific purpose or to be employed in a specific area of the body. As such, a number of different types and sizes of medical devices and connectors co-exist in a hospital setting. Inefficiently managing and/or finding the proper connector for each medical device or for each application can consume large amounts of time. The time elapsed during a search for a suitable connector increases the unavailability of the medical device, delays its application, and thereby decreases the number of procedures in which a medical device can be employed in a given time period. Thus, efficiently managing and/or quickly finding the correct connector for cleaning, disinfecting, and/or sterilizing a medical device can improve the availability of the medical device and improve the efficiency of the procedures employing the device. Accordingly, a storage apparatus and method are provided for identifying a position of an object.

Referring to FIG. 1, the figure illustrates a storage apparatus 102 for identifying a position of an object. The storage apparatus 102 can be any storage unit provided with a plurality of containers, such as a first container 104a, a second container 104b, and in certain examples, a third container 104c. Each container 104a-c may have a plurality of sidewalls that form a housing which forms a cavity within each container 104a-c. For example, first, second, and third housings 134a-c, respectively, each may comprise six sidewalls such as, a left sidewall, a right sidewall, a top sidewall, a bottom sidewall, a back sidewall, and a front sidewall. In certain examples, containers 104a-c may have housings 134a-c, respectively, that have a shared or common sidewall to an adjoining container. In other examples, the containers 104a-c may each be completely enclosed to themselves such that the housings 134a-c forming each adjoining container 104a-c, respectively, may each have separate sidewalls that result in double-walled separation. For example, as illustrated, first housing 134a of the first container 104a defines a first cavity 106a positioned within the first container 104a. Second housing 134b of the second container 104b may have a shared wall with first container 104a and has sidewalls that define a second cavity 106b positioned within the second container 104b. Third housing 134c of the third container 104c defines a third cavity 106c positioned within the third container 104c and includes a shared sidewall with second container 104b.

Figure 2A:
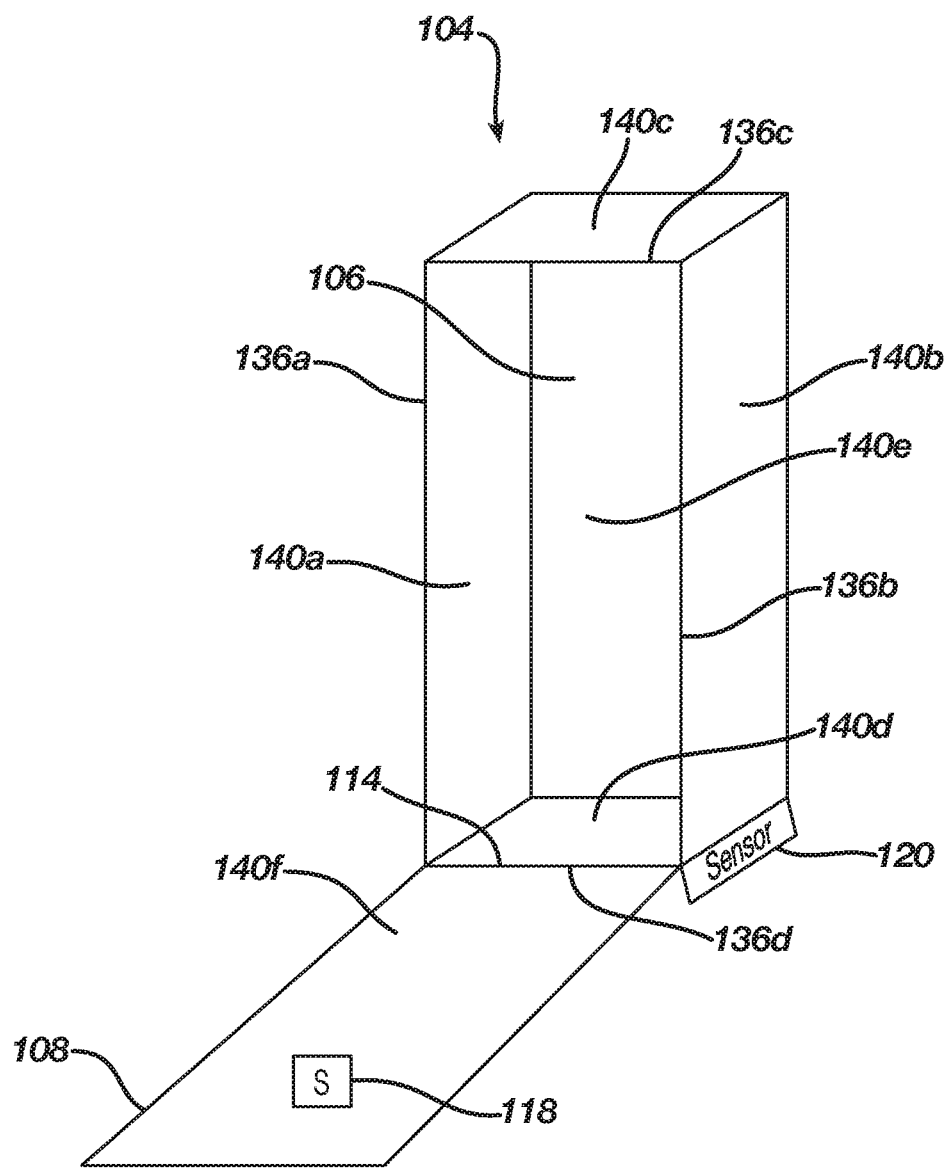
FIG. 2A is a perspective view of a container of the storage apparatus, illustrating a door in a first position.

As illustrated in FIG. 2A, which isolates one general example 104 of the containers 104a-c of FIG. 1, in certain examples, each housing 134a-c may comprise six sidewalls such as, a left sidewall 140a, a right sidewall 140b, a top sidewall 140c, a bottom sidewall 140d, a back sidewall 140e and a front sidewall 140f. The sidewalls 140a-f may form the container 104 which can be a rectangular box, having a cavity 106 therein. In certain examples, each sidewall 140a-f of housings 134a-c can be formed of one or more materials such as, but not limited to, metal and plastic.

Figure 2B:
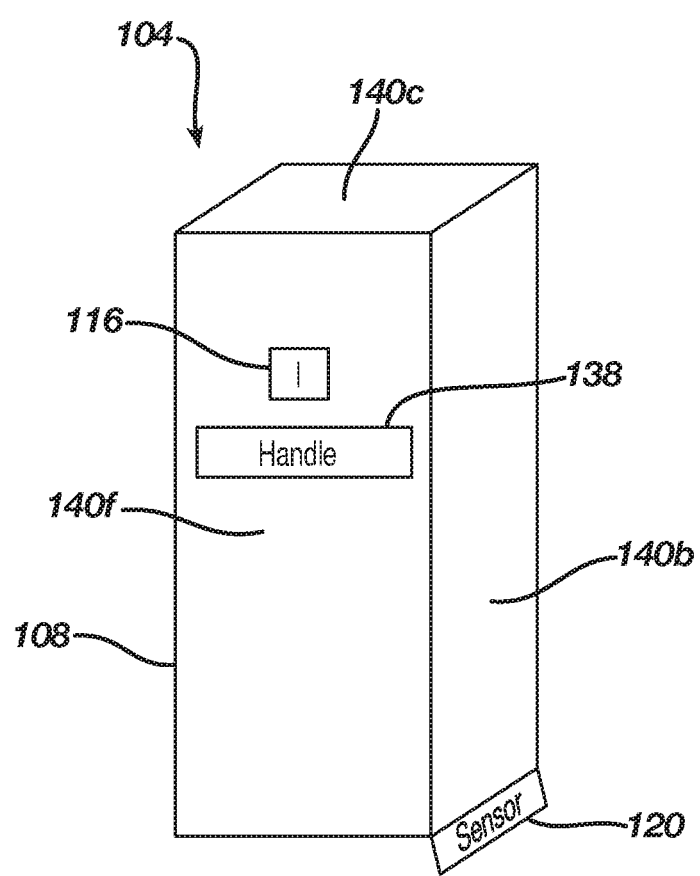
FIG. 2B is a perspective view of the container illustrating the door in a second position.

Each container 104a-c may be provided with a door to enclose the respective cavities 106a-c. Referring to FIGS. 2A-2B, in certain examples, the front sidewall 140f may also act as a door 108 which can enclose the cavity 106 within the respective housing 134a-c. For example, as illustrated, the container 104 may comprise a door 108 which can be configured to enclose the cavity 106. The door 108 may be operatively coupled to a pivot 114, such as a hinge, so that the door 108 can be moved from a first position, as illustrated in FIG. 2A, to a second position, as illustrated in FIG. 2B.

In certain examples, the first position of the door 108 is "open" and the second position of the door is "closed." In this configuration, when the door 108 is in the first position, the respective object 112a-c can be readily placed inside the cavity 106, and when the door 108 is in the second "closed" position, movement of the respective object 112a-c within the cavity 106 is generally limited. In certain examples, illustrated in FIG. 2A, when the door 108 is moved to the second position, the door 108 engages a first surface 136a of the left sidewall 140a, a second surface 136b of the right sidewall 140b, a third surface 136c of the top sidewall 140c, and/or a fourth surface 136d of the bottom sidewall 140d.

Figure 3:
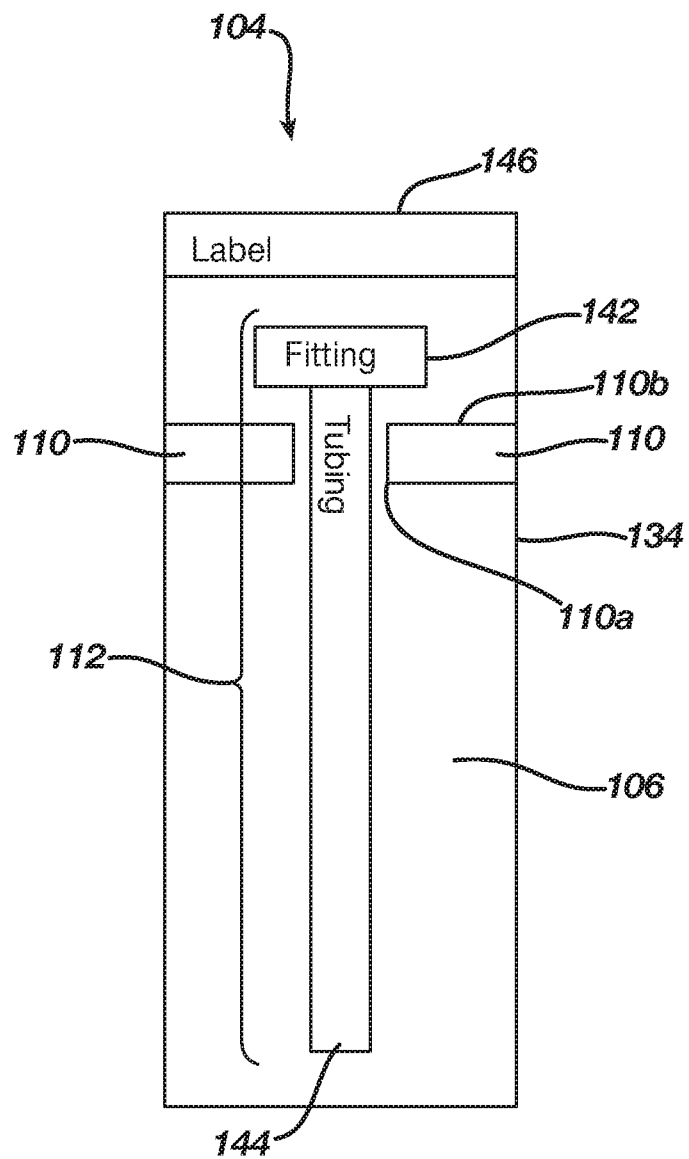
FIG. 3 is a plan view of the container illustrating a retainer of the container.

Referring again to FIG. 1, as illustrated, each container 104a-c may be sized and configured to receive an object 112a-c, respectively, within its respective cavity 106a-c. In particular, the first container 104a may be sized and configured to receive a first object 112a. Similarly, the second and third containers, 104b-c, may be configured to receive a second object 112b and a third object 112c, respectively. In certain examples, each container 104a-c can be configured to receive a plurality of objects that may be the same or different. In certain examples, the first object 112a, the second object 112b, and/or the third object 112c, may comprise a connector, such as a fitting 142 (FIG. 3). In examples where the object 112a-c is an endoscope, the connector is a device to connect the endoscope to a re-processing machine, such as, but not limited to, a tubing, a fitting, and combinations thereof.

A first visual indicator 116a, a second visual indicator 116b, and a third visual indicator 116c, when present, are configured to provide a visual signal that provides the position the respective object 112a-c in the containers 104a-c, the containers 104a-c themselves, or both. The visual signal may be, for example, a presentation of a message on the visual indicator, an illumination of the visual indicator, a start or cessation of illumination of the visual indicator, and a change in a state of illumination (color, intensity, lighting pattern, etc.). The visual indicators 116a-c may be, but are not limited to, a light emitting diode (LED), a laser diode, an incandescent bulb, a fluorescent bulb, a high-intensity discharge bulb, and a visual display.

Figure 5:
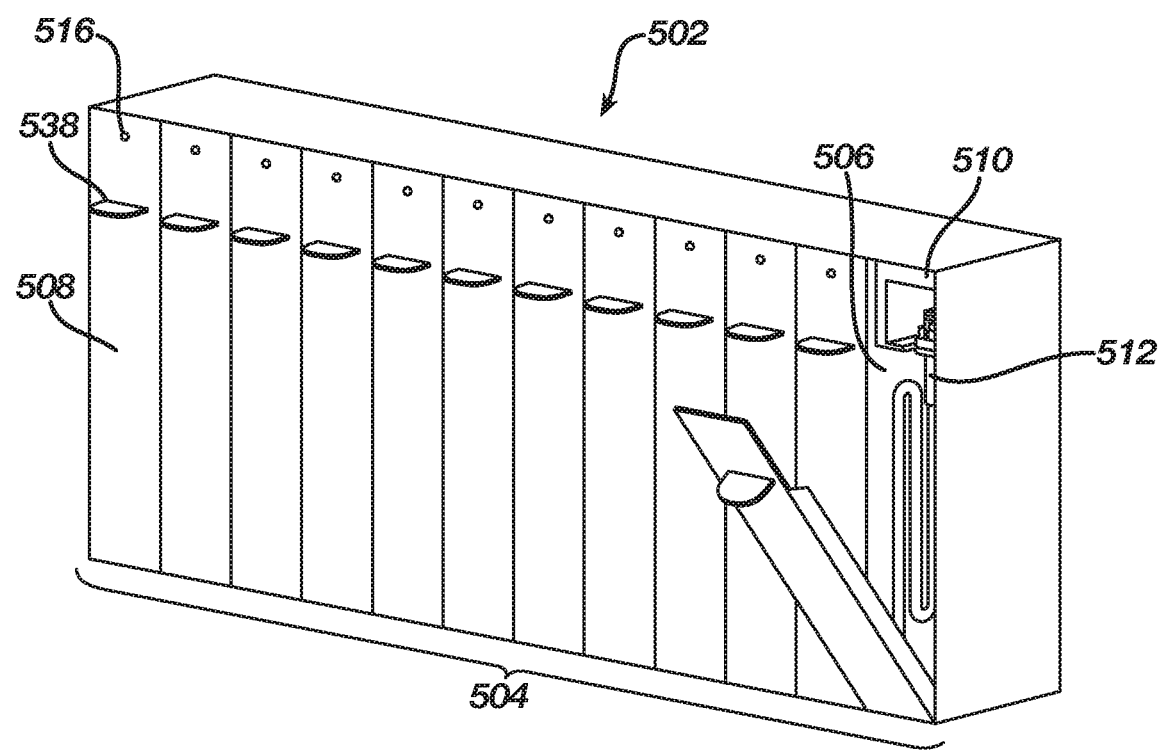
FIG. 5 is a perspective view of a storage apparatus with a plurality of containers.

The visual indicators 116a-c may be operatively coupled to each respective container 104a-c. In certain examples, as illustrated in FIG. 2B and FIG. 5, a visual indicator 116, 516 is operatively coupled to the door 108, 508. In certain other examples, the visual indicators 116a-c can be physically separate from each container 104a-c and positioned proximal to each container 104a-c such as, next to, on top of, or below a respective container 104a-c. For example, the visual indicators 116a-c may be a portion of a portable electronic device. Accordingly, the positioning of the visual indicators 116a-c is for illustration purposes only and should not be considered limiting.

Each visual indicator 116a-c can be configured to indicate a position of the object 112a-c in a respective corresponding container 104a-c, the container 104a-c itself, or both. For example, in order to indicate the position of the first container 104a and/or first object 112a, the first visual indicator 116a can provide a first visual signal. Similarly, in order to indicate the position of the second container 104b, the second visual indicator 116b can provide a second visual signal. In order to indicate the position of the third container 104c, the third visual indicator 116c can provide a third visual signal. Each visual signal may be the same as or different than another visual signal. For example, the first, second, and third visual signals may each be the same as each another, and can be, for example, an illumination of the respective visual indicator 116a-c. In certain examples, the first, second, and/or third visual signals may be different such that illumination of at least one of the respective visual indicators 116a-c is in a different color than the rest of the visual indicators. Accordingly, each visual indicator 116a-c can be configured with various visual signals.

As illustrated, a programmable hardware device (PHD) 122 may be provided with functionality to identify the position of a select container(s) 104a-c and/or a select object(s), such as the objects 112a-c, which corresponds to an identifier. The PHD 122 may be any PHD know to those of ordinary skill in the art, and may be a hardware device configured with a processor operatively coupled to a memory. The identifier may be, for example, a name, a word, a number, a symbol, a character, a sequence of characters, and a hash. For example, the identifier may be, but is not limited to, a serial number, a part number, a model number, a part name, a name of a manufacturer, and a brand name. In certain examples, the identifier is associated with the identity of a secondary object 126. The secondary object 126, may be, but is not limited to, an endoscope. Accordingly, the identifier may be associated with a secondary object 126 and the identifier may be utilized to provide the identity of the secondary object 126 to the PHD 122.

The PHD 122 can be configured with an input device 124 which is configured to receive the identifier. The input device 124 may be, but is not limited to, a radio-frequency identification (RFID) reader, a barcode scanner, a microphone, and a keypad. In certain examples, the input device 124 is a RFID reader and the identifier is present on an RFID tag 128 associated with the secondary object 126. The RFID reader can interrogate the RFID tag 128 and determine the identifier based on the interrogation. In certain examples, the RFID tag 128 can actively send the identifier to be received by the RFID reader. In certain examples, the input device 124 can be a barcode scanner which may be configured to scan a barcode, such as a barcode 130 associated with the secondary object 126. The barcode 130 encodes the identifier in a visual pattern which is interpreted by the barcode scanner and communicated to the PHD 122. In certain examples, the input device 124 is a keypad, such as, a numeric-only keypad or an alphanumeric keypad. The identifier can be provided to the keypad by an operator. Accordingly, the input device 124 receives the identifier associated with the secondary object 126, such as an endoscope.

Regardless of how the identifier is received, the PHD 122 can utilize the position of the visual indicators 116a-c and a visual signal to communicate a message to an operator such as, a position of a container corresponding to the identifier. For example, the PHD 122 may receive a first identifier which corresponds to the first container 104a. Upon receipt of the first identifier, the PHD 122 indicates the first container 104a corresponds to the received first identifier by utilizing the first visual indicator 116a to provide the first visual signal. Similarly, upon receipt of a second identifier which corresponds to the second container 104b, the PHD 122 indicates the second container 104b corresponds to the received second identifier by utilizing the second visual indicator 116b to provide the second visual signal. In certain examples, the second identifier corresponds to the second container 104b and the third container 104c thus, the PHD 122 indicates the second and third containers, 104b and 104c, respectively, correspond to the received second identifier by utilizing the second and third visual indicators, 116b and 116c, respectively, to provide the second and third visual signals, respectively. Accordingly, identifiers can correspond to any number of containers.

The PHD 122 can utilize different visual signals to indicate which container(s) is relevant to the identifier and how the container(s) is relevant. The secondary object 126 associated with the identifier can have different features which require different objects in order to prepare and/or process the secondary object 126 through a cleaning, disinfecting, and/or sterilizing procedure. For example, the first object 112a may be needed to prepare the first feature and the second object 112b may be needed to prepare the second feature. In order to communicate which object corresponds to which feature, the PHD 122 can utilize different visual signals to indicate how the container is relevant. For example, the PHD 122 can utilize the first visual indicator 116a to create a fifth visual signal, such as illuminating the first visual indicator 116b a first color to indicate the first object 112a is in the first container 104a and the first object 112a corresponds to the first feature. Similarly, the PHD 122 may utilize the second visual indicator 116b to create a second visual signal, such as illuminating the second visual indicator 116b a second color, different than the first color, to indicate the second object 112b is in the second container 104b and the second object corresponds to the second feature. Thus, utilizing visual signals, the position of an object(s) which corresponds to the secondary object 126 can be quickly identified and how the object(s) is relevant to the secondary object 126 can be quickly determined.

In order to determine which container(s) and/or object(s) corresponds to an identifier, in certain examples, the PHD 122 has a data structure 132. The data structure 132 may be stored in the memory within the PHD 122 or in a memory external to the PHD 122. The data structure 132 may be a database which has a list of identifiers and a corresponding list of containers. In certain examples, the database 132 can additionally have, but is not limited to, a listing of object(s) within a container(s), a listing of object type(s), a tare weight of a container(s), a quantity of access(es) to a container(s), a quantity of access(es) to an object, a listing of secondary object(s), a corresponding feature(s) of the secondary object(s), and a visual signal type. Accordingly, the database 132 can be utilized in order to determine which container(s) corresponds to the identifier and which visual signal should be used to identify the container(s).

Upon receipt of the identifier, the PHD 122 is configured to search the listing of identifiers in the database 132 to find an entry matching the received identifier. When the matching entry is found, the PHD 122 finds a container(s) within the list of containers corresponding to the matching entry. The found container may directly correspond to the matching entry in the database 132 and/or indirectly correspond to the matching entry by having an object that corresponds to the matching entry. Regardless of how the corresponding container(s) is determined, the PHD 122 indicates the position of the corresponding container(s) utilizing at least one of the visual indicators 116*a-c* to create a visual signal.

In certain examples, switches are operatively in communication with each container 104*a-c*. Referring to FIGS. 2A-B, for example, a switch 118 can be operatively in communication with the container 104. The switch 118 can be provided with functionality to determine if the container 104 has been accessed. For example, the switch 118 may be configured to engage with a handle 138 which may be operatively coupled to the door 108. The switch 118 may be changeable between a first state and a second state based on a force applied to and/or removed from the handle 138. For example, when accessing the container 104, a force may be applied to the handle 138 and the switch 118 may change from the first state to the second state responsive to the applied force. The state change can be communicated to and/or measured by the PHD 122. Based on the state change, the PHD 122 can determine the container 104 has been accessed. In certain examples, the switch 118 may be, but is not limited to, a contact switch and a magnetic switch, which sense a position change in the door 108 between the first position and the second position. Accordingly, the switch 118 may be utilized to determine whether the container 104 has been or is being accessed.

In certain examples, the PHD 122 ceases identification of the corresponding container(s) after the PHD 122 determines the corresponding container(s) has been accessed by utilizing at least one visual indicator 116*a-c* to create the visual signal and/or stop the visual signal. For example, if the first visual indicator 116*a* was illuminated to indicate the position of the first container 104*a*, the PHD 122 may cease the illumination of the first visual indicator 116*a* after the first container 104*a* is accessed. Similarly, if the first visual indicator 116*a* was changed from the first color to the second color to indicate the position of the first container 104*a*, the PHD 122 may change the first indicator back to the first color after the first container 104*a* is accessed.

In certain examples, the PHD 122 is provided with functionality to determine a level of utilization of the containers 104*a-c* and/or the object(s) within the containers 104*a-c*. For example, the PHD 122 may track the quantity of access(es) to each container 104*a-c* utilizing the database 132. The PHD 122 may compare the quantity of accesses to a threshold value for utilization, which, in certain examples, is stored in database 132. If the PHD 122 determines that the quantity of accesses to a select object(s) and/or container(s) is greater than or equal to the threshold value, the PHD 122 determines the select object(s) and/or container(s) are over-utilized. Similarly, if the PHD 122 determines that the quantity of accesses to a select object(s) and/or container(s) is less than the threshold value, the PHD 122 determines the select object(s) and/or container(s) are not over-utilized. The PHD 122 can communicate the result of the level of utilization determination utilizing the visual indicators 116*a-c* to create a visual signal and/or the PHD 122 can store the result of the level of utilization determination in the database 132.

In certain examples, a load sensor can be operatively coupled to each container 104*a-c*. For example, as illustrated in FIGS. 2A-B, a load sensor 120 can be operatively coupled to the container 104. The load sensor 120 is provided with functionality to determine a weight of the container 104. For example, the load sensor 120 can output a signal to the PHD 122 which is variable depending upon the weight within the container 104 measured by the load sensor 120. The PHD 122 can utilize the signal to determine the weight of the container 104. Accordingly, the PHD 122, supported by a respective load sensor, can determine the weight of the containers 104*a-c*.

The PHD 122 may utilize the determined weight to determine the level of occupancy in a respective container(s) 104*a-c*. For example, based on the determined weight, the PHD 122 can determine that the first container 104*a* is less than full (e.g., vacant, does not contain an object, contains less than a select quantity, etc.), and the PHD 122 can indicate a state of the first container 104*a* as less than full utilizing the first visual indicator 116*a* to create a sixth visual signal. The sixth visual signal may be changing the color of the first visual indicator 116*a* to a third color to indicate the first container 104*a* is less than full. In certain examples, the sixth visual signal may be ceasing the illumination of the first visual indicator 116*a* to indicate the first container 104*a* is less than full. In certain examples, based on the determined weight, the PHD 122 can determine that the first container 104*a* is occupied (e.g., contains at least one object, contains equal to or more than a select quantity, full, etc.) and the PHD 122 can indicate the state of the first container 104*a* as occupied utilizing the first visual indicator 116*a* to create a seventh visual signal. The seventh visual signal may be turning the first visual indicator 116*a* to a fourth color to indicate the first container 104*a* is occupied. In certain examples, the seventh visual signal may be initiating illumination of the first visual indicator 116*a* to indicate the first container 104*a* is occupied. Accordingly, various visual signals may be used to indicate the level of occupancy of the containers 104*a-c*.

The PHD 122 may determine the level of occupancy of each container 104*a-c* by comparing the determined weight to a weight stored in the database 132. For example, each container 104*a-c* may be listed in the database 132 and have a corresponding tare weight (e.g., empty container weight). The PHD 122 may compare the determined weight of the respective container(s) 104*a-c* measured via a load sensor, such as load sensor 120, to the tare weight of the respective container(s) 104*a-c*. Based on the comparison, the PHD 122 may determine the level of occupancy of the respective container(s) 104*a-c*. For example, if the determined weight of the respective container(s) 104*a-c* is greater than the respective tare weight, the PHD 122 may determine that the respective container(s) 104*a-c* is occupied. If the determined weight of the respective container(s) 104*a-c* container is similar to and/or equal to the tare weight, the PHD 122 may determine that the respective container(s) 104*a-c* is less than full, such as vacant. Accordingly, the database 132 may facilitate determining the level of occupancy of within the container(s) 104*a-c*.

In certain examples, each container 104*a-c* can be provided with a retainer. For example, as illustrated in FIG. 3, a retainer 110 is positioned in a cavity 106 of a container 104 and operatively coupled to at least one of the sidewalls of the housing 134 of the container 104. The retainer 110 is configured with a shape to hold the object 112 in a first position within the cavity 106. The retainer 110 can limit movement of the object 112 within the cavity 106 and the retainer 110 can provide physical support for an orientation and/or a position of the object 112 within the cavity 106. For example, the object 112 may comprise a fitting 142 operatively coupled to a tubing 144. The fitting 142 may have a first diameter which is larger than a second diameter of an opening 110*a* of the retainer 110 such that the fitting 142 can be limited from moving through the opening 110*a*. Thus, while limited from moving through the opening 110*a*, the fitting 142 may engage a first surface 110*b* of the retainer 110. The engagement between the fitting 142 and the first surface 110b can support the first position of the object 112. The tubing 144 may have a third diameter which is less than the second diameter, such that the tubing 144 can move throughout the opening 110a. Accordingly, each container 104a-c may be provided with a retainer in order to support the position of the objects 112a-c, respectively.

In certain examples, each container 104a-c can be provided with a label. For example, the container 104 can be physically marked with a label 146. The label may be, but is not limited to, a container identity, an object identity, a serial number, and a model number. The position and size of the label 146 are for illustration purposes only and should not be considered limiting.

Figure 4:
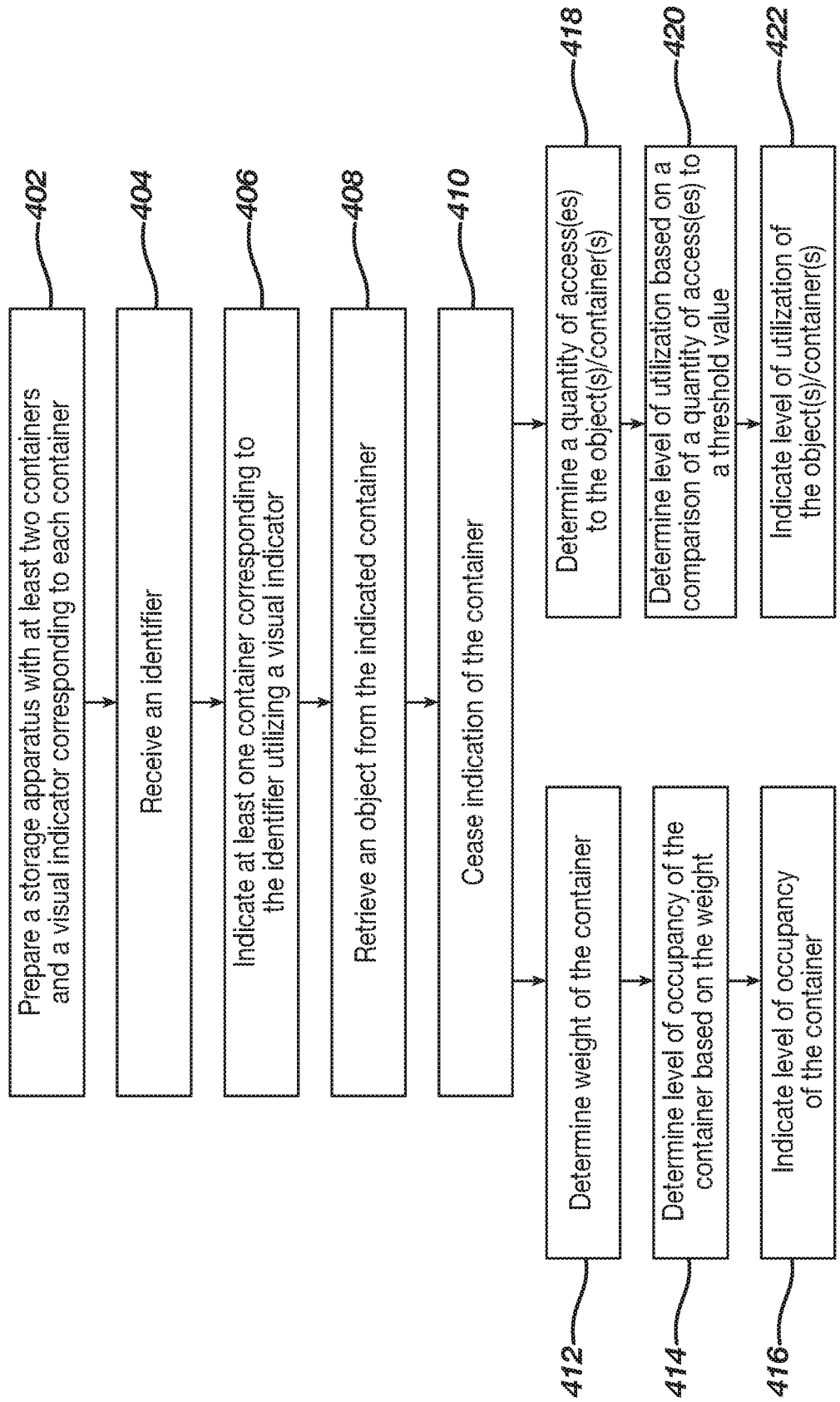
FIG. 4 is a flow chart illustrating a method to retrieve an object based on an identified positioned.

Referring to FIG. 4, a flow chart is provided illustrating a method to retrieve an object based on an identified positioned. As illustrated, a storage apparatus is prepared 402. The storage apparatus has at least two containers and each container is configured with a cavity to receive one or more first objects. The storage apparatus has a visual indicator corresponding to each container. Each visual indicator can be operatively coupled to a respective container and/or proximally positioned to a respective container.

An identifier, which can be associated with a secondary object, is received 404. In certain examples, the identifier is received from an RFID tag associated with an endoscope. In certain examples, the receiving of the identifier includes scanning a barcode associated with an endoscope and determining the identifier from the scanning. In certain examples, the identifier is input into a keypad. Responsive to receipt of the identifier, a position of at least one of the containers corresponding to the identifier is indicated 406. The indication is facilitated by utilizing at least one of the visual indicators, which correspond to the corresponding container(s), to provide a first visual signal.

At least one first object is retrieved from the indicated container(s) 408. The first object(s) may comprise at least one device to connect an endoscope to a re-processing machine. The device may be selected from the group consisting of a tubing, a fitting, and combinations thereof. The first object(s) may be used to prepare and/or process the secondary object through a cleaning, disinfecting, and/or sterilizing procedure. In certain examples, the first visual signal may indicate how the first object(s) may be used to prepare and/or process the secondary object. In certain examples, the indication of the container ceases after the indicated container is accessed by removing the first visual signal 410. Accordingly, the first object(s) may be retrieved from the indicated container and can be utilized in cleaning, disinfecting, and/or sterilizing the secondary object.

In certain examples, a weight of one or more of the containers is determined 412. Based on the determination of the weight, the level of occupancy of the container is determined 414. In certain examples, the determined weight is compared to a tare weight. Based on the comparison, the level of occupancy is indicated by utilizing at least one visual indicator to provide a visual signal 416. For example, if the weight of the container is greater than the tare weight, the container is indicated as occupied. In certain examples, if the weight of the container is similar to and/or equal to the tare weight, e.g. vacant, no indication is performed. Accordingly, the visual signal may indicate the level of occupancy of the container based on the weight of the container.

In certain examples, a level of utilization of at least one of the first object(s) and/or container(s) is determined by determining a quantity of accesses to the first object(s) and/or container(s) 418. The level of utilization is determined by comparing the quantity of access to the first object(s) and/or container(s) to a threshold value for utilization 420. The level of utilization of the first object(s) and/or container(s) is indicated by utilizing at least one visual indicator to provide a visual signal 422. For example, if the utilization is equal to or greater than the threshold value for utilization, the first object(s) and/or container(s) are indicated as over-utilized. In certain examples, the utilization is less than the threshold value for utilization and no indication is performed. Accordingly, the visual signal may indicate the level of utilization of the first object(s)/ container(s) based on the quantity of accesses to the container.

Referring to FIG. 5, the figure illustrates a storage apparatus 502 for identifying a position of an object and/or a container. The storage apparatus 502 has a plurality of containers 504 adjacently positioned to each other. The quantity of containers is for illustration purposes only and should not be considered limiting. Each container 504 is configured with a retainer 510 positioned in a cavity 506 of the respective container 504. The retainer 510 is configured with a shape to hold an object 512 in a first position within the cavity 506. Additionally, each container 504 is configured with a visual indicator 516 and a handle 538 positioned on a door 508. The storage apparatus 502 can indicate a position of objects 512 in the containers 504, the containers 504 themselves, or both utilizing the visual indicators 516 to provide a visual signal.

As described herein, the visual signal(s) may communicate various information, such as a position of a container(s) and/or object(s), how a container(s) and/or object(s) is relevant to the identifier(s)/secondary object(s), the occupancy level of the container(s), and the utilization level of the container(s) and/or object(s). The information can enable efficient management of the container(s) and/or object(s), quick location of the container(s) and/or object(s), and rapid recognition of how to use the object(s). Thus, the efficiency in preparing the secondary object, such as an endoscope, for cleaning, disinfecting, and/or sterilizing can be enhanced.

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more examples has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various embodiments and with various modifications as are suited to the particular use contemplated. It is intended that the claims submitted herewith define the overall scope.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A storage apparatus for identifying the position of an object in a sterilization process, wherein the object comprises at least one device to connect an endoscope to a re-processing machine, the apparatus comprising:
    at least two containers, each container having a cavity configured to receive the object;
    at least one visual indicator corresponding to each container; and
    a programmable hardware device (PHD) configured to receive an identifier,
        responsive to receipt of the identifier, the PHD configured to indicate:
            (a) a position of at least one of the containers that corresponds to the identifier utilizing the visual indicator; and
            (b) the at least one container is relevant to a first feature of the endoscope utilizing the visual indicator to create a visual signal.

2. The apparatus of claim 1, wherein each visual indicator is selected from the group consisting of a light emitting diode and a visual display.

3. The apparatus of claim 1, wherein the PHD is configured with at least one input device selected from the group consisting of: a radio-frequency identification (RFID) reader, a barcode scanner, and a keypad.

4. The apparatus of claim 3, wherein the RFID reader is configured to receive the identifier from an RFID tag associated with the endoscope.

5. The apparatus of claim 3, wherein the barcode scanner is configured to scan a barcode associated with an endoscope and the PHD is configured to determine the identifier from the scan.

6. The apparatus of claim 1, wherein the PHD is configured to cease to indicate the position of the at least one of the containers after the at least one of the containers is accessed.

7. The apparatus of claim 6, further comprising a switch configured to communicate to the PHD that the at least one of the containers has been accessed.

8. The apparatus of claim 1, wherein the PHD further comprises a database having a list of identifiers corresponding to a list of the containers.

9. The apparatus of claim 1, further comprising at least one load sensor corresponding to each container, the PHD configured to utilize the load sensor to determine a weight of one or more of the containers.

10. The apparatus of claim 9, wherein:
    responsive to a determination that the one or more of the containers is vacant based on the determined weight, the PHD is configured to indicate that the one or more of the containers is vacant utilizing the visual indicator.

11. The apparatus of claim 1, wherein:
    the PHD is configured to determine utilization of at least one of the object in one or more of the containers; and
    responsive to a determination that the determined utilization is equal to or greater than a threshold, the PHD is configured to indicate that the at least one of the object is over-utilized.

12. The apparatus of claim 1, wherein the device is selected from the group consisting of a tubing, a fitting, and combinations thereof.

13. The apparatus of claim 1, wherein the at least one visual indicator is positioned proximal to each container.

14. The apparatus of claim 1, wherein responsive to receipt of the identifier, the PHD is configured to:
indicate a position of at least two of the containers that correspond to the identifier, including a first container having a first cavity configured to receive a first object utilizing a first visual indicator and a second container having a second cavity configured to receive a second object utilizing a second visual indicator; and
indicate the first object is relevant to a first feature of the endoscope utilizing the first visual indicator to create a first visual signal and the second object is relevant to a second feature of the endoscope utilizing the second visual indicator to create a second visual signal different than the first visual signal.

15. The apparatus of claim 1, further comprising a retainer operatively coupled to at least one of the containers, the retainer comprises an opening configured to receive at least a portion of the object, wherein the retainer is configured to physically support an orientation and/or a position of the object.

16. A method for retrieving an object that is, or will be, used in a sterilization process, wherein the object comprises at least one device to connect an endoscope to a re-processing machine, the method comprising:
preparing a storage apparatus having at least two containers, each container configured with a cavity to receive the object, the storage apparatus having at least one visual indicator corresponding to each container;
receiving an identifier;
responsive to receipt of the identifier, indicating a position of at least one of the containers that corresponds to the identifier utilizing the visual indicator and the at least one container is relevant to a first feature of the endoscope utilizing the visual indicator to create a visual signal; and
retrieving at least one of the object from the container as indicated by the visual indicator.

17. The method of claim 16, further comprising:
receiving the identifier from an RFID tag associated with the endoscope.

18. The method of claim 16, wherein receiving the identifier further comprises:
scanning a barcode associated with an endoscope; and
determining the identifier from the scanning.

19. The method of claim 16, further comprising
ceasing indication of the position of the at least one of the containers after the at least one of the containers is accessed.

20. The method of claim 16, further comprising determining a weight of one or more of the containers.

21. The method of claim 20, further comprising:
responsive to determining the at least one container is vacant based on the determining of the weight, indicating the at least one container is vacant utilizing the visual indicator.

22. The method of claim 16, further comprising:
determining utilization of at least one of the object in one or more of the containers; and
responsive to a determination that the utilization is equal to or greater than a threshold, indicating the at least one of the object is over-utilized.

23. The method of claim 16, wherein the device is selected from the group consisting of a tubing, a fitting, and combinations thereof.

* * * * *